(12) United States Patent
Zimenkov et al.

(10) Patent No.: US 7,782,454 B2
(45) Date of Patent: Aug. 24, 2010

(54) UNIVERSAL MULTIDETECTION SYSTEM FOR MICROPLATES

(75) Inventors: Oleg Zimenkov, South Burlington, VT (US); Xavier Amouretti, Essex Junction, VT (US); Robert M. Gifford, Starksboro, VT (US); Mark R. Kennedy, South Burlington, VT (US); Michael Kontorovich, Colchester, VT (US); Ben Norris, Monkton, VT (US); Richard N. Sears, Jericho, VT (US); Dan Venditti, Colchester, VT (US); Christopher Many, Highgate, VT (US)

(73) Assignee: BTI Holdings, Inc., Winooski, VT (US)

( * ) Notice: Subject to any disclaimer, the term of this patent is extended or adjusted under 35 U.S.C. 154(b) by 641 days.

(21) Appl. No.: 11/802,831

(22) Filed: May 25, 2007

(65) Prior Publication Data

US 2008/0191149 A1      Aug. 14, 2008

Related U.S. Application Data (60) Provisional application No. 60/900,976, filed on Feb. 13, 2007.

(51) Int. Cl.
*G01J 3/44* (2006.01)
(52) U.S. Cl. .................................. 356/301; 356/318
(58) Field of Classification Search .................. 356/301, 356/316, 318
See application file for complete search history.

(56) References Cited

U.S. PATENT DOCUMENTS

| | | | |
|---|---|---|---|
| 3,843,257 A * | 10/1974 | Wooten | ........................ 356/316 |
| 3,999,864 A * | 12/1976 | Mutter | ........................ 356/448 |
| 4,516,856 A | 5/1985 | Popelka | |
| 4,531,834 A | 7/1985 | Nogami | |
| 4,730,922 A | 3/1988 | Bach et al. | |
| 5,290,513 A | 3/1994 | Berthold et al. | |
| 5,933,232 A | 8/1999 | Atzler et al. | |
| 6,042,785 A | 3/2000 | Harju | |
| 6,071,748 A | 6/2000 | Modlin et al. | |
| 6,097,025 A | 8/2000 | Modlin et al. | |
| 6,144,455 A | 11/2000 | Tuunanen et al. | |
| 6,187,267 B1 | 2/2001 | Taylor et al. | |
| 6,232,608 B1 | 5/2001 | Giebeler et al. | |
| 6,236,456 B1 | 5/2001 | Giebeler et al. | |
| 6,307,626 B1 * | 10/2001 | Miles et al. | ................. 356/301 |
| 6,313,471 B1 | 11/2001 | Giebeler et al. | |
| 6,316,774 B1 | 11/2001 | Giebeler et al. | |

(Continued)

*Primary Examiner*—Kiet T Nguyen
(74) *Attorney, Agent, or Firm*—Sughrue Mion, PLLC (57) ABSTRACT

An apparatus and a method for optically analyzing a sample are provided. The apparatus includes a first optical device that transmits a narrow waveband of light and has a first filter and a first monochromator that provide different paths for the narrow waveband of the light. The apparatus may also include a light source that generates the light as broadband excitation light, in which case the first optical device transmits a narrow waveband of the broadband excitation light through the first filter or the first monochromator. Further, the apparatus may include a second optical device that directs the narrow waveband of the broadband excitation light onto the sample and receives emission light from the sample, a third optical device that transmits a narrow waveband of the emission light, and a detector that converts the narrow waveband of the emission light into an electrical signal.

10 Claims, 10 Drawing Sheets

U.S. PATENT DOCUMENTS

| | | |
|---|---|---|
| 6,466,316 B2 | 10/2002 | Modlin et al. |
| 6,469,311 B1 | 10/2002 | Modlin et al. |
| 6,538,735 B1 | 3/2003 | Duebendorfer et al. |
| 6,654,119 B1 | 11/2003 | Gould et al. |
| 6,822,741 B2 | 11/2004 | Aronkytö et al. |
| 6,825,921 B1 | 11/2004 | Modlin et al. |
| 6,965,105 B2 | 11/2005 | Oldham et al. |
| 6,982,434 B2 | 1/2006 | Smith et al. |
| 6,985,225 B2 | 1/2006 | Bechem et al. |
| 2002/0043626 A1 | 4/2002 | Booker et al. |
| 2002/0070349 A1 | 6/2002 | Hoyt |
| 2003/0030797 A1 | 2/2003 | Palladino et al. |
| 2003/0042428 A1 | 3/2003 | Peukert et al. |
| 2003/0219754 A1 | 11/2003 | Olesky et al. |
| 2004/0057870 A1 | 3/2004 | Isaksson et al. |
| 2004/0113095 A1 | 6/2004 | Peltie et al. |
| 2004/0200979 A1 | 10/2004 | Reel |
| 2005/0012929 A1 | 1/2005 | Booker et al. |
| 2005/0046849 A1 | 3/2005 | Cromwell et al. |
| 2005/0062969 A1 | 3/2005 | Harju et al. |
| 2005/0105080 A1 | 5/2005 | Landlinger |
| 2005/0218338 A1 | 10/2005 | Wulf et al. |
| 2006/0066857 A1 | 3/2006 | Ok et al. |

\* cited by examiner

UNIVERSAL MULTIDETECTION SYSTEM FOR MICROPLATES

CROSS-REFERENCE TO RELATED APPLICATION

This application claims priority from U.S. Provisional Patent Application No. 60/900,976, filed on Feb. 13, 2007, in the United States Patent and Trademark Office, the disclosure of which is incorporated herein in its entirety by reference.

BACKGROUND OF THE INVENTION

1. Field

Apparatuses and methods consistent with the present invention relate to detection systems, including the detection of fluorescence, absorbance, and chemiluminescence in samples placed in the wells of microplates.

2. Description of the Related Work

Multiple analytical instruments are used in laboratories to evaluate samples under test that are placed into vessels of various shapes. In the past twenty years, a microplate format has become very popular, as it lends itself to testing many samples on a single matrix-style receptacle. The first detection systems for microplates were absorbance readers. Later dedicated fluorometers were developed, followed by instruments to measure chemiluminescence.

The range of assay chemistries and labeling technologies continues to grow. Currently employed detection methods include absorbance, multiplexed fluorescence and chemiluminescence, fluorescence polarization (FP), time-resolved fluorescence (TRF), fluorescence resonance energy transfer (FRET), quenching methods, and specially designed labels with intensity and spectral responsiveness to environmental conditions. Along with this range of detection methods, users are conjugating an ever-growing array of organic and inorganic labels for targets, ranging from small-molecule drug candidates to proteins and nucleic acids, and to subcellular structures and cells.

Figure 1:
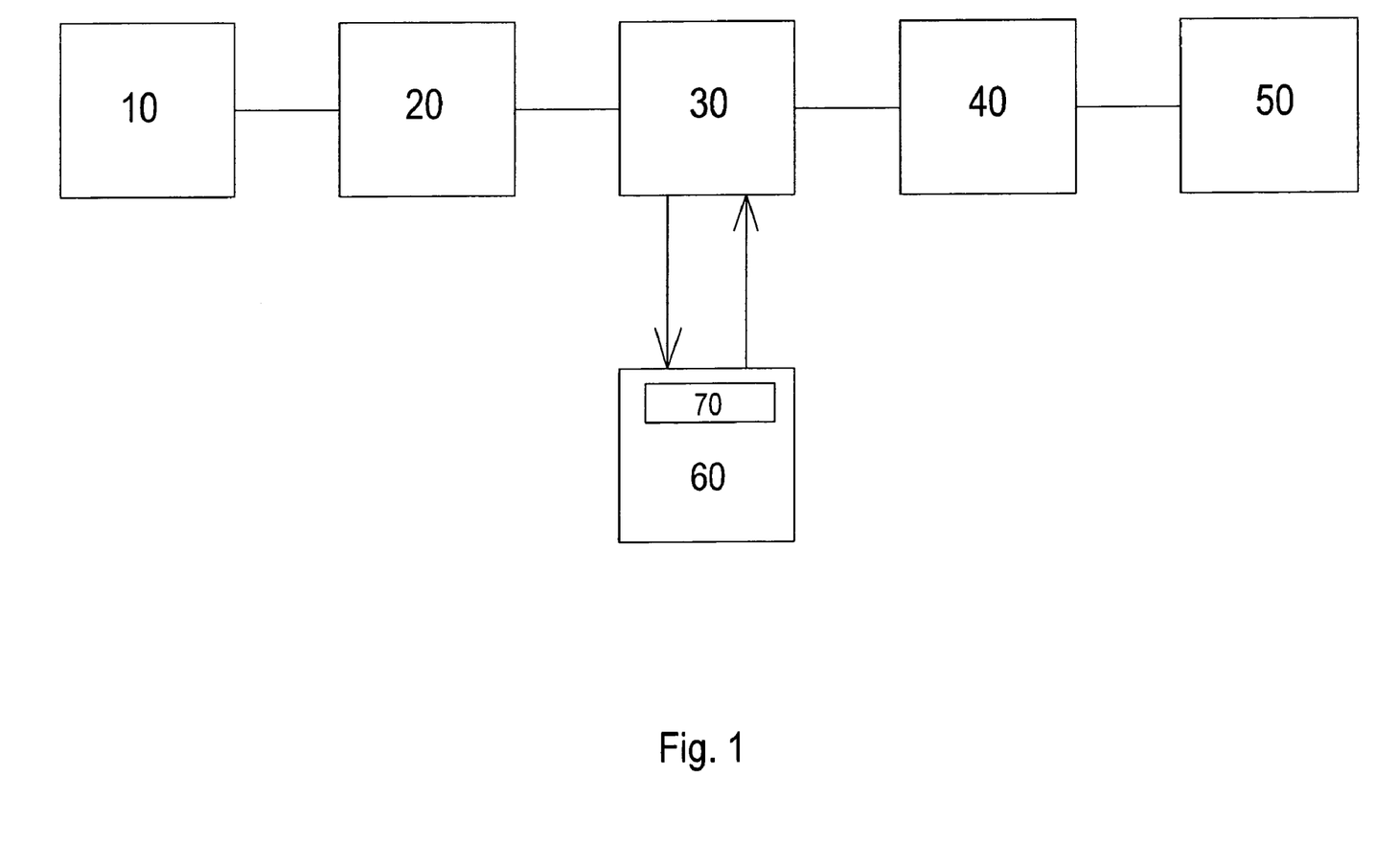
FIG. 1 illustrates a general structure of a multimode detection system.

FIG. 1 illustrates the general structure of a related art multimode detection system. As shown in FIG. 1, a typical system comprises a light source 10, an excitation spectral device 20, an optical module 30, a measurement chamber 60 with samples 70, an emission spectral device 40, and a detector 50. There are two distinct types of related art multimode detection systems: filter-based units and monochromator-based units.

Filter-based units, when offered with high quality filters in combination with dichroic mirrors, allow for measurements with very low detection limits. This is mainly due to a high signal level, which is achieved with the filters, in combination with a high signal-to-noise ratio, which is achieved by a high level of blocking of the unwanted radiation around the desired waveband. The transmittance of filters is routinely over 50%, and this high level of transmittance can be achieved independent of the wavelength. Therefore, a very broad spectral range can be covered equally well from the deep ultraviolet (UV) to the infrared (IR), and the bandpass of the filter can be tailored to the specific application.

However, the filter-based unit cannot obtain a spectral scan for excitation or emission of the substance under investigation. A user must know upfront what substance he or she is working with and order an appropriate filter set. In addition, when working in the deep UV, filters tend to degrade when exposed to the UV radiation of the light source, due to solarization. Also, maintaining libraries of filters for the full range of labels is prohibitively expensive, and appropriate combinations are often not readily available for a given label, conjugation chemistry, target molecule, and assay condition. Further, the effects of these conditions are not always predictable based on the nominal spectra of the basic label.

Monochromator-based instruments offer a high level of flexibility in terms of choosing the wavelengths and obtaining scans of excitation and emission spectra, thus allowing the user to work with unknown substances. This also permits optimization of the measurements for perturbations to the spectra of labels due to assay conditions, conjugation chemistries, and target molecules. Additionally, when working with real biological or biochemical samples, interfering signals from other sample components may require optimization of excitation and emission wavelengths for the exact assay conditions.

The monochromators used in modern instruments are usually based on diffraction gratings, and use a flat grating for dispersion and concave mirrors for focusing light, or concave gratings that combine dispersive and focusing functions. Monochromators require order sorting filters to separate high spectral orders, but in the range from 200 nm to about 380 nm, no order sorting filters are needed. Therefore, there is no need for filters that withstand UV radiation, and the solarization problem is avoided.

However, the response of the monochromator is not constant across the wavelength range. One can obtain a system with a good signal in the UV, the visible, or the IR; however, one cannot obtain a system with a good signal in all of the wavelength ranges in the same monochromator-based unit. A usual compromise is to optimize the excitation monochromator in the UV and to optimize the emission monochromator in the visible or IR, because the wavelength of the emission light shifts to the right with respect to the wavelength of the excitation light.

In order to obtain low detection limits, the monochromator must have very low stray light. A traditional way to achieve this in the monochromator-based system is to employ two stage monochromators. These are called double monochromators, and contain two single monochromators placed in series. While this does result in very low stray light, the penalty is a dramatic decrease in signal, especially in spectral regions where the response of the single stage monochromator is already low. There are several instruments in the field based on this method, such as the Tecan INFINITE and the Thermo VARIOSKAN.

In terms of performance, the filter-based units achieve significantly lower detection limits in fluorescence intensity applications across the full spectral range, and work significantly better with techniques such as TRF, FP, and Homogeneous Time-Resolved Fluorescence (HTRF), all of which require the strong signal provided by the filter-based units. On the other hand, the monochromator-based units provide the flexibility of choosing any wavelength and the ability to obtain a spectral scan, at the expense of lower sensitivity.

U.S. Pat. No. 6,313,471 describes a method that combines bandpass filters and monochromators in series in a detection system. In this method, the bandpass filter acts as a crude first stage monochromator. The instrument splits the full spectral range of interest into several regions corresponding to the number of filters employed, and blocks radiation from adjacent regions by using additional filters. The single stage monochromator that follows the bandpass filters then selects the wavelength of interest from this prefiltered range.

However, with a limited number of prefiltered regions, this method is limited in flexibility. If both the excitation and emission wavelengths fall into one region, the method is not effective in achieving low stray light or high performance.

True spectral scanning is not readily accomplished with this method. This limits its utility for spectral measurement and optimization under conditions of fine spectral perturbation.

There is currently no related art instrument that combines the best of filter-based measurements and monochromator-based measurements in a single unit, and allows a user to choose between the two measurement types. A need exists for a single multidetection system that combines the low detection limits and assay methodology flexibility of filter-based units with the wavelength flexibility and superior UV performance of the monochromator-based units. This instrument could provide a user with a full flexibility in terms of assay type and wavelength selection.

SUMMARY

Exemplary embodiments of the present invention overcome the above disadvantages and other disadvantages not described above. Also, the present invention is not required to overcome the disadvantages described above, and an exemplary embodiment of the present invention may not overcome any of the problems described above.

According to an aspect of the present invention, there is provided an apparatus for optically analyzing a sample, which includes a first optical device that transmits a narrow waveband of light and includes a first filter and a first monochromator that provide different paths for the narrow waveband of the light. The apparatus may also include a light source that generates the light as broadband excitation light, wherein the first optical device transmits a narrow waveband of the broadband excitation light and blocks other wavebands of the broadband excitation light through the first filter or the first monochromator; a second optical device that directs the narrow waveband of the broadband excitation light onto the sample and receives emission light from the sample; a third optical device that transmits a narrow waveband of the emission light; and a detector that converts the narrow waveband of the emission light into an electrical signal; wherein the third optical device includes a second filter and a second monochromator that provide alternative paths for the narrow waveband of the emission light.

According to another aspect of the present invention, there is provided a method of optically analyzing a sample, including the step of transmitting a narrow waveband of light through a first filter or a first monochromator, wherein the first filter and the first monochromator provide alternative paths for the narrow waveband of the light. The method may further include the steps of generating the light as broadband excitation light; transmitting a narrow waveband of the broadband excitation light through the first filter or the first monochromator; directing the narrow waveband of the broadband excitation light onto the sample; receiving emission light from the sample; transmitting a narrow waveband of the emission light; and converting the narrow waveband of the emission light into an electrical signal; wherein the step of transmitting the narrow waveband of the emission light includes transmitting the narrow waveband of the emission light through a second filter or a second monochromator; the first filter and the first monochromator provide alternative paths for the narrow waveband of the broadband excitation light; and the second filter and the second monochromator provide alternative paths for the narrow waveband of the emission light.

According to another aspect of the present invention, there is provided an optical apparatus for separating emission light from excitation light, which includes a holder that moves in a direction perpendicular to a plane defined by optical axes of the excitation light and the emission light; a first linear polarizer with a polarization axis perpendicular to the plane defined by the optical axes of the excitation light and the emission light; a second linear polarizer with a polarization axis parallel to the plane defined by the optical axes of the excitation light and the emission light; a third linear polarizer with a polarization axis parallel to the polarization axis of the first linear polarizer; and a partially reflective and partially transparent mirror that directs the excitation light toward a sample and receives the emission light from the sample; wherein the holder can be moved to position at least one of the first linear polarizer, the second linear polarizer, the third linear polarizer, and the mirror in a path of at least one of the excitation light and the emission light.

According to another aspect of the present invention, there is provided a light source for optically analyzing a sample, which includes a first parabolic reflector that collimates light from a first lamp; and an off-axis parabolic reflector that focuses the collimated light from the first lamp onto a focal point. The light source may also include a second parabolic reflector that collimates light from a second lamp; and a lens that focuses the collimated light from the second lamp onto the focal point; wherein the off-axis parabolic reflector moves out of an optical path of the collimated light from the second lamp if the second lamp is emitting light.

According to another aspect of the present invention, there is provided an optical apparatus for separating emission light from excitation light, which comprises a first lens that directs a first narrow waveband of excitation light onto a sample and a second lens that receives a first emission light from the sample, wherein optical axes of the first lens and the second lens form a V shape in which the sample is positioned at a bottom of the V shape. The optical apparatus may further include a third lens that directs a second narrow waveband of excitation light onto the sample and a fourth lens that receives a second emission light from the sample; wherein optical axes of the third lens and the fourth lens form a V shape in which the sample is positioned at a bottom of the V shape; and none of the optical axes of the first lens, the second lens, the third lens, and the fourth lens are parallel to each other.

BRIEF DESCRIPTION OF THE DRAWINGS

The above and other aspects of the present invention will become more apparent by describing in detail exemplary embodiments thereof with reference to the attached drawings, in which.

DETAILED DESCRIPTION OF EXEMPLARY EMBODIMENTS OF THE INVENTION

Figure 2:
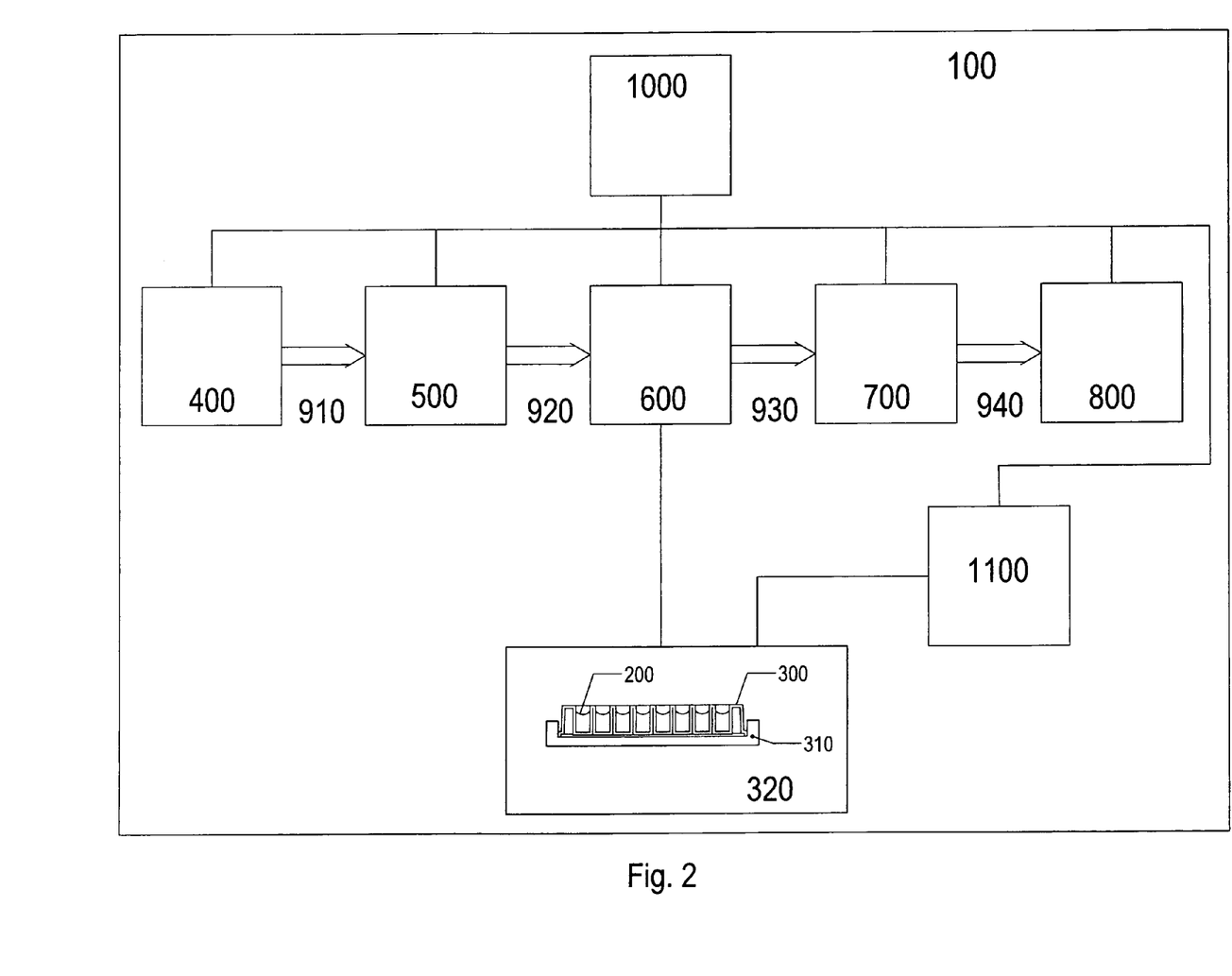
FIG. 2 illustrates certain components of a Universal Multidetection System (UMS) according to an exemplary embodiment of the present invention.

FIG. 2 illustrates certain components of a Universal Multidetection System (UMS) 100 according to an exemplary embodiment of the present invention. As shown in FIG. 2, samples are dispensed into the array of microwells 200 in the microplate 300. The microplate 300 is transported by the carriage 310 into the measurement chamber 320, which may be incubated, and is positioned sequentially for measurements. The light source 400 generates excitation light. The excitation spectral device 500 selects and transmits a narrow band of the excitation light. The waveband is typically between 5 and 40 nm wide. The excitation-emission separation device 600 directs the excitation light to the microwells 200, and then separates the emission light generated in the sample within the microwells 200 from the excitation light. The excitation-emission separation device 600 transmits the emission light to the emission spectral device 700, which transmits a narrow band of the emission light. The emission spectral device 700 should be configured to transmit as much emission light as possible, while blocking as much excitation light as possible and maximizing the signal-to-noise ratio. The detector 800 converts the emission light into an electrical signal. Although the light source 400, the excitation spectral device 500, the excitation-emission separation device 600, the emission spectral device 700, and the detector 800 are shown as separate modules, they can also be combined in a variety of ways.

As shown in FIG. 2, relay devices 910, 920, 930, and 940 provide optical connections between the light source 400, the excitation spectral device 500, the excitation-emission separation device 600, the emission spectral device 700, and the detector 800. The controller 1000 stores emission signals from samples in the microplate 300, analyzes the emission signals, computes parameters categorizing the optical measurements, and sends commands to the light source 400, the excitation spectral device 500, the excitation-emission separation device 600, the emission spectral device 700, or the detector 800. The commands can instruct the light source 400, the excitation spectral device 500, the excitation-emission separation device 600, the emission spectral device 700, or the detector 800 to change an internal parameter. For example, the commands can instruct the excitation spectral device 500 or the emission spectral device 700 to use one internal device instead of another internal device. Further, an optional dispenser 1100 delivers reagent to the microwells 200.

Figure 3:
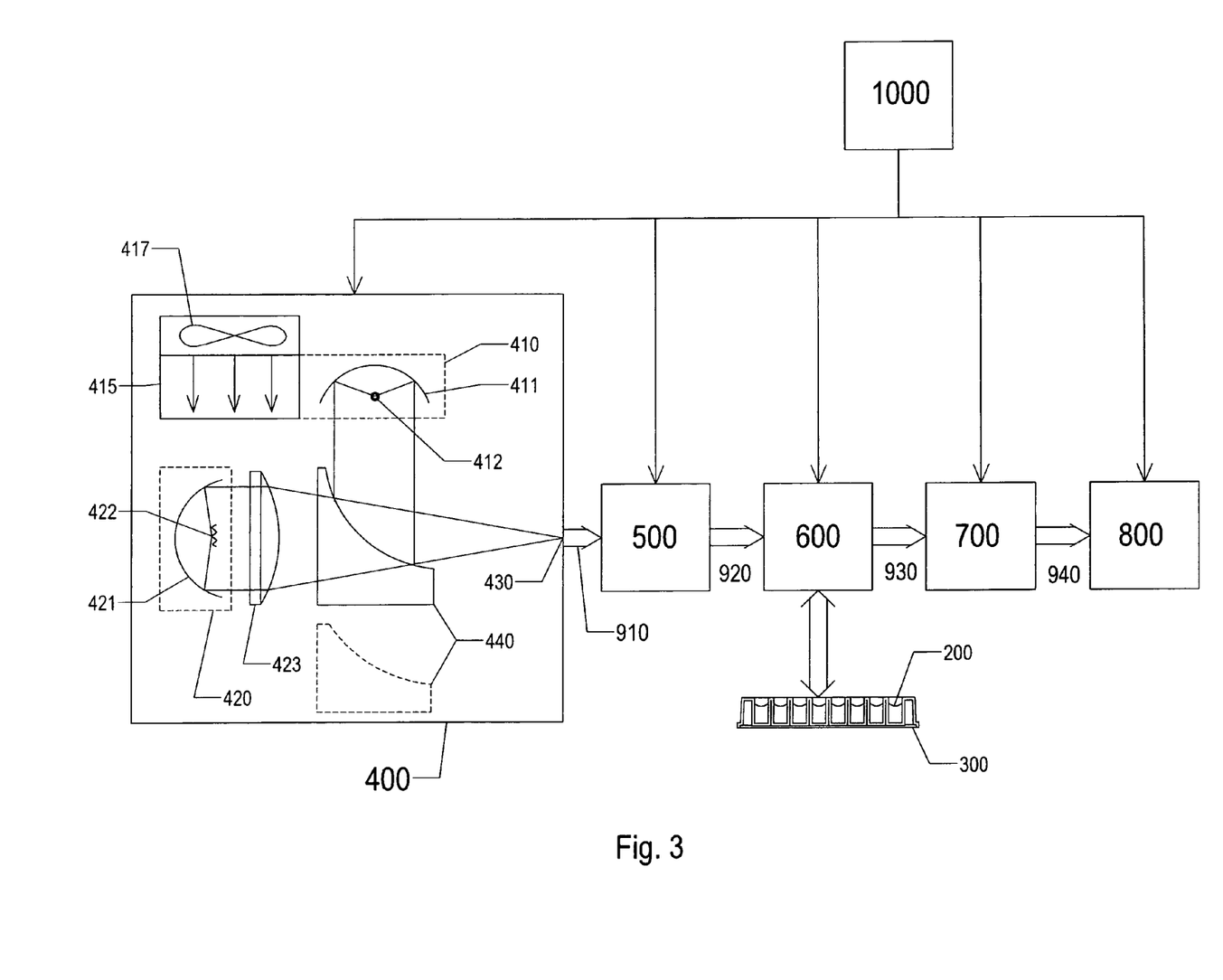
FIG. 3 illustrates a light source according to an exemplary embodiment of the present invention.

FIG. 3 illustrates the structure of the light source 400 according to an exemplary embodiment of the present invention. In a preferred embodiment, the light source 400 comprises only two light generating devices: a Xenon flash lamp 410 and a Tungsten lamp 420. In other embodiments the light source 400 may comprise a Xenon continuous wave lamp, a light emitting diode (LED), a laser, or any other light-generating device.

Tungsten sources are very stable, and their radiation extends from blue in the visible spectrum to the far IR, and peaks around 1 µm. They are most suitable for measurements in the visible and IR regions of the spectrum. In contrast, Xenon flash sources deliver most of their radiation in the deep UV, UV, and short visible spectral ranges. In addition, Xenon flash sources provide a very fast burst of light, lasting for several microseconds with a fast decay, and are therefore suitable for time resolved measurements in modern multidetection systems.

Figure 5:
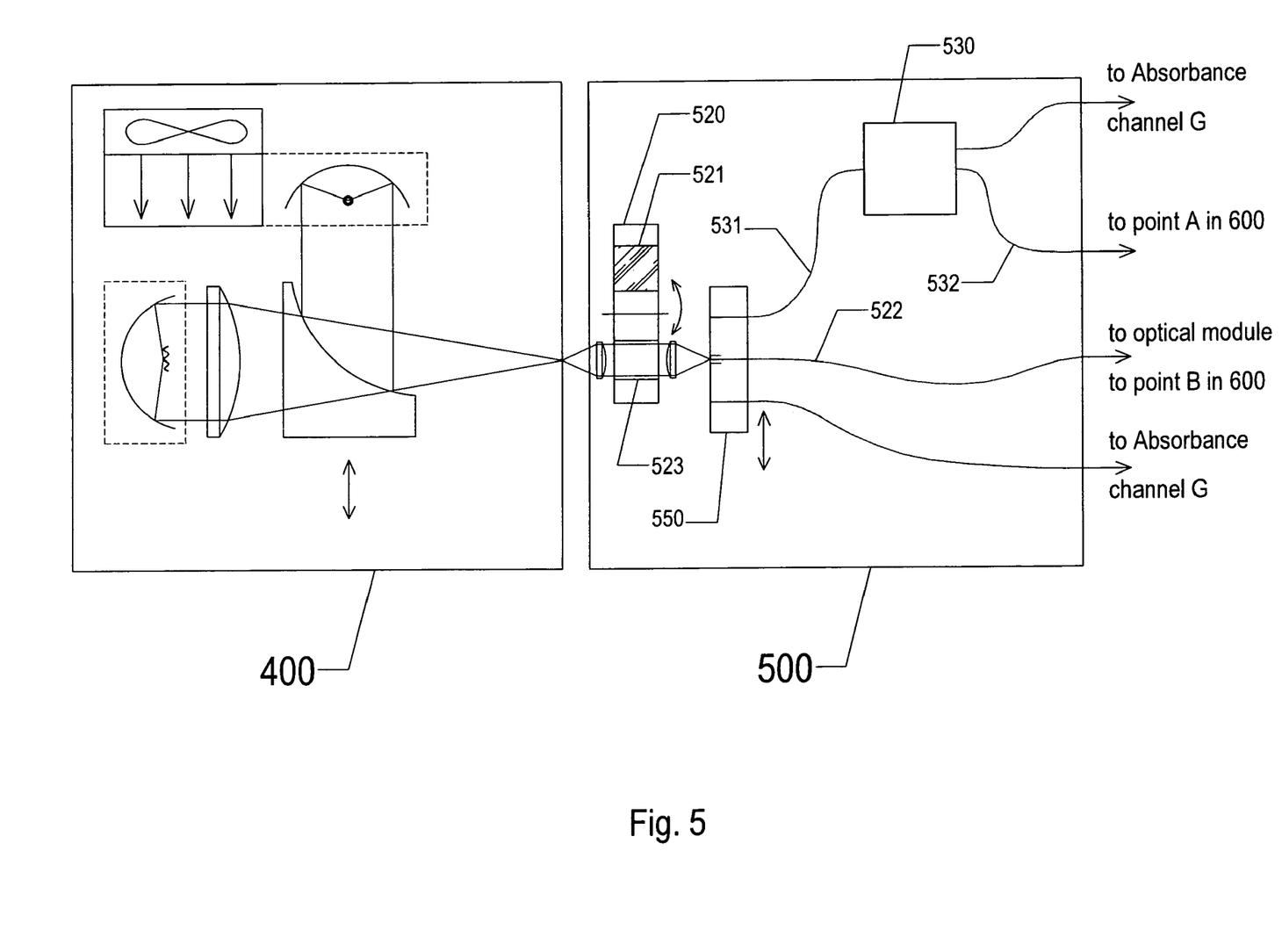
FIG. 5 shows optical connections between the light source, the excitation spectral device, and the excitation-emission separation device according to an exemplary embodiment of the present invention.

The Xenon flash lamp 410 has a parabolic reflector 411 positioned such that the arc 412 of the lamp 410 is located near the focal point of the reflector 411, providing an essentially collimated beam from the reflector 411. The Tungsten lamp 420 has a parabolic reflector 421 positioned such that the filament 422 of the lamp 420 is located near the focal point of the reflector 421, providing an essentially collimated beam from the reflector 421. FIG. 3 shows that a lens 423 may be used to focus the beam from the reflector 421 onto the exit portal 430 of the light source 400. As shown in FIG. 5, relay optics may be used to focus the beam onto the entrance of an optical fiber. Alternatively, the lens 423 may focus the beam from the reflector 421 directly onto the entrance of an optical fiber within the excitation spectral device 500.

The movable off-axis parabolic reflector 440 has two working locations. In the first location, depicted by a solid line in FIG. 3, the reflector 440 reflects and focuses light from the reflector 411. In the second location, depicted by a dashed line in FIG. 3, the reflector 440 stays out of the way of light from the reflector 421. This arrangement allows light from either lamp to be focused at the same location. Further, the fan 417 directs air across the fins 415 of a cooling extrusion for the Xenon source 410 and onto the Tungsten source 420. This arrangement allows both sources to share a single cooling system.

The arrangement of two light sources in close proximity to each other, with their optical axes offset, and preferably at an angle of approximately 90 degrees to each other, allows for a very compact illumination system with a shared cooling system. The use of parabolic reflectors around the light sources, in combination with off-axis parabolic reflectors, results in very highly efficient coupling of light from the arc and filament into the system. Here the final focusing point of both light sources is the same. This system allows a more compact arrangement than a system which utilizes separate light source compartments with separate exit light points for each compartment, thus requiring a mechanical movement of the optical relay system to switch between sources.

Figure 4:
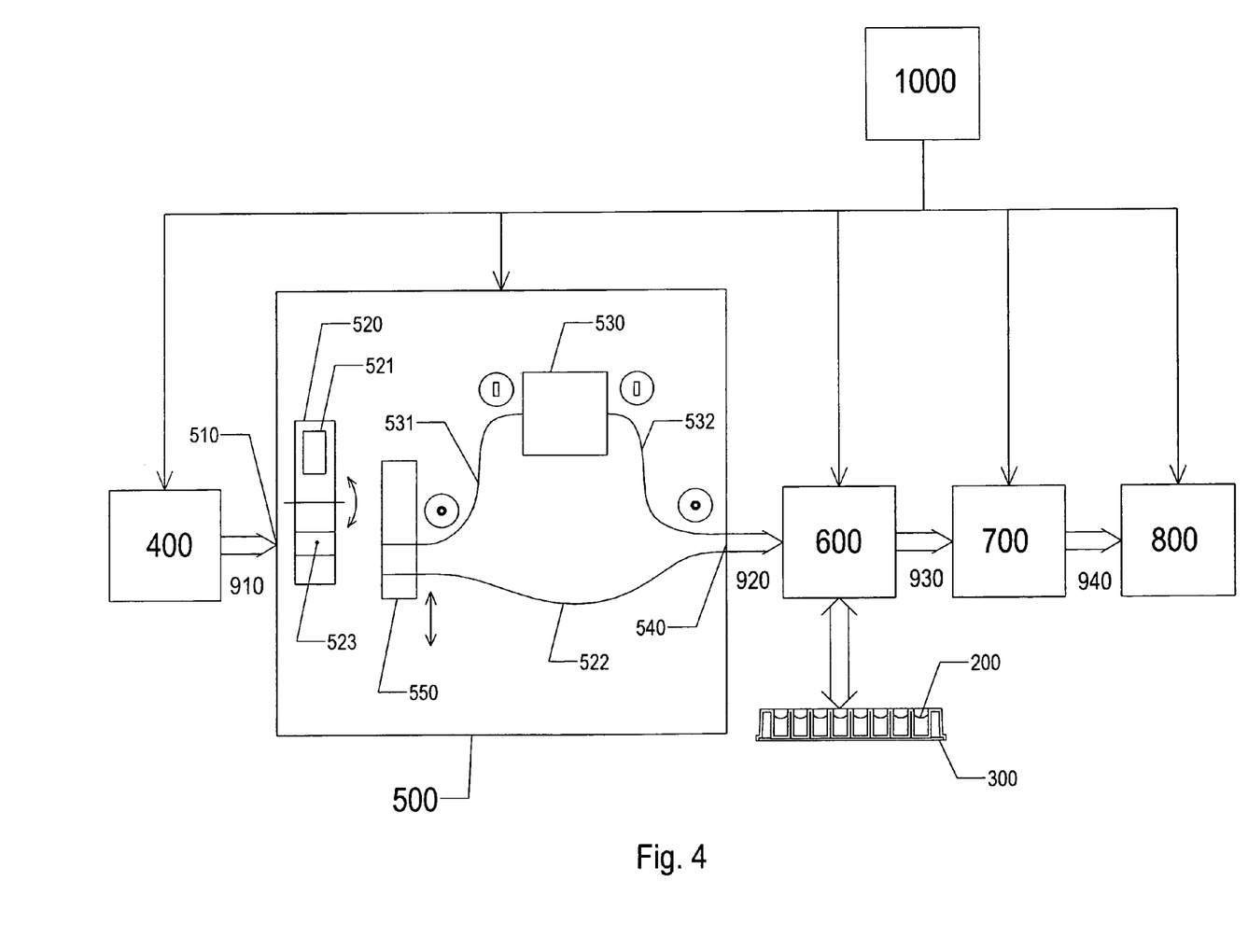
FIG. 4 illustrates an excitation spectral device according to an exemplary embodiment of the present invention.

FIG. 4 illustrates the structure of the excitation spectral device 500 according to an exemplary embodiment of the present invention. The exit portal 430 of the light source 400 is in close proximity to the input portal 510 of the excitation spectral device 500. The relay device 910 is unfilled space inside the UMS 100.

In a preferred embodiment, the excitation spectral device 500 has two spectral selection devices, which differ by the physical technology by which they separate light with different wavelengths. The first device is a filter selection device 520, which has a variety of user-replaceable filters 521. The second device is a double monochromator 530.

As shown in FIG. 4, the light exiting the light source 400 via the exit port 430 is directed to the entry point 510 of the excitation spectral device 500. Light entering the excitation spectral device 500 is then directed to the exit port 540 of the excitation spectral device 500 along one of two paths.

The first path directs the light through one of the filters 521 in the filter selection device 520, which transmits a narrow band of the light. The light then propagates through optical fiber 522 to the exit port 540. The second path bypasses the filters 521 by directing the light through hole 523 in the filter selection device 520. The light then continues via optical fiber 531, which accepts a circular image of the arc or filament spot from the light source 400 formed at the entry port 510, and shapes the light spot into a slit shape to match it to the input slit of the double monochromator 530. The monochromator 530 selects a narrow band of the light, and then the optical fiber 532 changes the shape of the light from the exit slit shape of the monochromator 530 into a circular shape that resembles the shape of a microwell 200.

The light path selector 550 can move relative to the filter selection device 520, providing the ability to guide light to the exit port 540 that was spectrally selected by the filters 521 or the monochromator 530. FIG. 5 shows the optical connections between the light source 400, the excitation spectral device 500, and the excitation-emission separation device 600 in greater detail.

Figure 6:
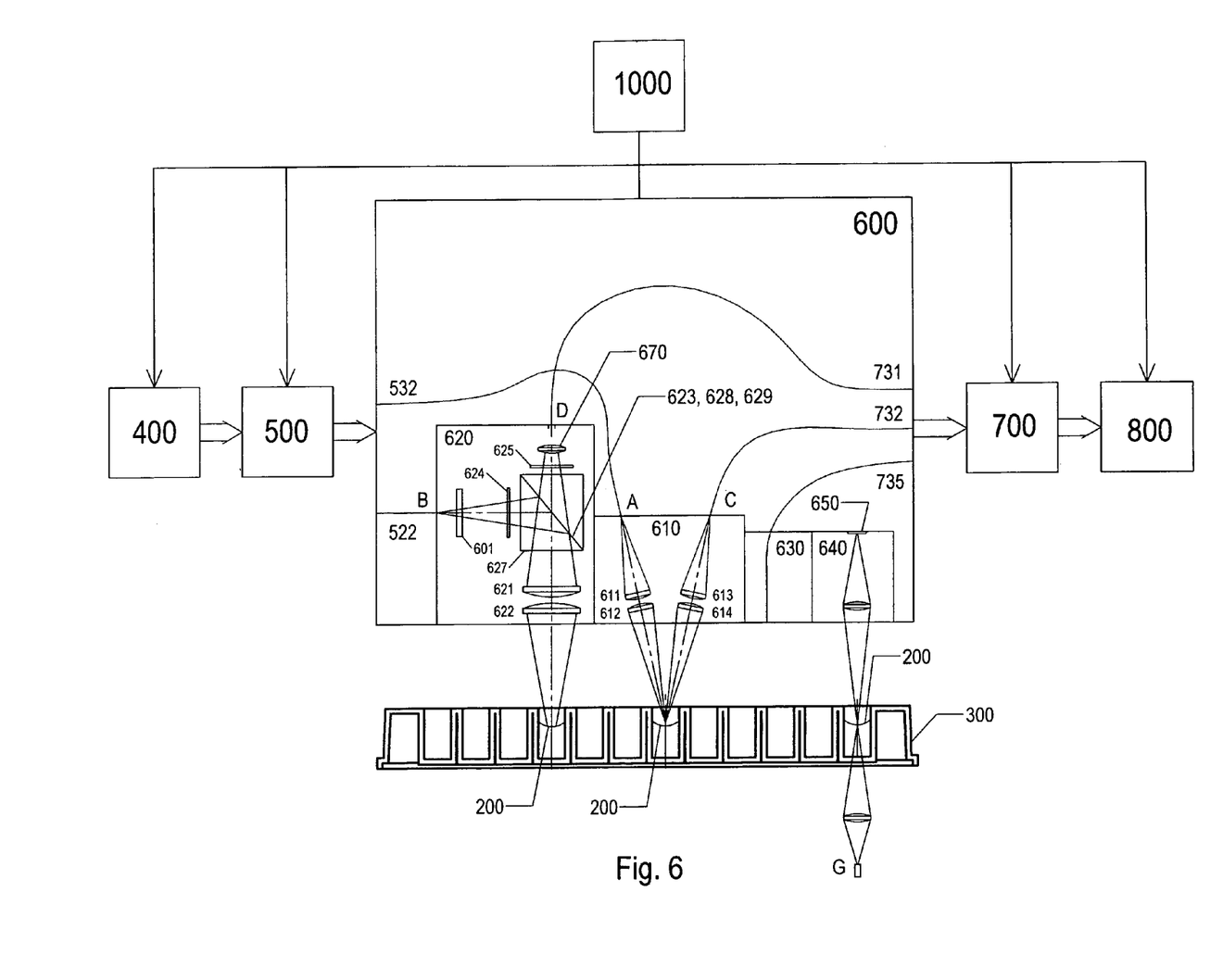
FIG. 6 illustrates an excitation-emission separation device according to an exemplary embodiment of the present invention.

FIG. 6 illustrates the structure of the excitation-emission separation device 600 according to an exemplary embodiment of the present invention. The general purpose of the excitation-emission separation device 600 is to irradiate the sample with excitation light and/or gather emission light from the sample. The excitation-emission separation device 600 can be positioned above the microwell 200 as shown in FIG. 6, or below the microwell 200. Also, the Universal Multidetection System 100 can include two excitation-emission separation devices 600, one of which is positioned above the microwell 200, and the other of which is positioned below the microwell 200. This arrangement enables measurements of the same microwell 200 with a filter-based system and a monochromator-based system from both the top and the bottom.

In a preferred embodiment, several light paths may be used, based on the measurement technique. For absorbance measurements, the excitation and emission light are preferably collinear. As shown in FIG. 6, the absorbance measurements are conducted in block 640, in which the microwell 200 is illuminated with excitation light from below at point G. This excitation light may come from the monochromator 530 or the filter selection device 520, as shown in FIG. 5. A detector 650 is placed on the opposite side of the microwell 200 to capture emission light that passes through the sample.

For luminescence measurements, no excitation light is required, and only emission light is gathered from the sample by the excitation-emission separation device 600. In block 630, a single fiber optic bundle 735 is used to maximize the light gathering capability of the system and thus improve the signal.

For fluorescence measurements, two optical paths are available to irradiate the sample with excitation light and to gather emission light from the sample. These paths can be optimized to further enhance the overall system performance.

Block 620 depicts a first optical path for fluorescence measurements, which can use a partially reflective mirror or a dichroic mirror so that excitation light and emission light are collinear when entering and exiting the sample, respectively. Light is delivered to Block 620 by the optical fiber 522. The movable aperture 601 has several openings with diameters preferably ranging from approximately 1.5 mm to 4 mm, and is placed in front of the guide fiber 522. An image of the opening placed in front of the optical fiber 522 is formed in the microwell 200 by lenses 621 and 622. The size of the opening of the movable aperture 601 is selected to fill the microwell 200 as completely as possible with light, while preventing light from entering adjacent microwells and causing cross-talk.

The light is reflected by a partially transmitting mirror 623 on a movable holder 627. More than one mirror can be placed onto the holder 627. Some mirrors can be dichroic mirrors to improve the signal, as all excitation light is reflected towards the microwell 200, and all emission light is transmitted towards exit fiber. The dichroic mirrors can also improve the signal-to-noise ratio of the measurement system, as residual excitation light that reaches the microwell 200 and is reflected by the meniscus lens is blocked from reaching the exit fiber. The emission light from the microwell 200 is gathered onto the fiber optic bundle 731 by lenses 621, 622, and 670. A collective lens 670 in front of the fiber optic bundle 731 assures that emission light from the full depth of the microwell 200 is collected, thus maximizing the system signal.

The high energy collection characteristics of the system assure low detection limits and allow for various levels of fluid to produce acceptable results without the need to refocus the optical system based on the fluid volume. This is in contrast with, for example, the confocal style measurements described in U.S. Pat. No. 6,097,025, which uses a confocal optical system that collects light only from the small portion of the microwell.

In a preferred embodiment, linear polarizers 624 and 625 are added to the holder 627, and the same motion that positions appropriate mirrors in the light path also can be used to select polarizers for fluorescence polarization measurements. This eliminates the need for a separate mechanism to switch the polarizers, and thus improves the reliability of the system.

Block 610 depicts a second optical path for fluorescence measurements, which uses a tilted V arrangement of optics for direct well illumination and light gathering. This allows the system to channel the full amount of light from the fiber optic 532 into the microwell 200. The numerical aperture of the optics 611 and 612 is matched to the fiber optic 532 for this purpose. The cone of excitation light enters the microwell 200 and excites the contents of the microwell 200 via the first leg of the V. The emission light is collected by the second leg of the V. The numerical aperture of lenses 614 and 613 matches the exit fiber optic 732. The V is tilted with respect to the vertical plane to direct excitation light that is specularly reflected from the surface of the microwell 200 away from the light collecting leg of the V. Therefore, this arrangement introduces a spatial separation of emission and excitation light in addition to the spectral separation, and significantly improves the signal-to-noise ratio. This tilted V arrangement can also be used to conduct fluorescence polarization measurements.

The entry ports A and B of the excitation-emission separation device 600 accept fiber bundles from the excitation spectral device 500. Fibers can be positioned to direct light that is spectrally separated by filters in the excitation spectral device 500 into input B of Block 620. Fibers can also be positioned to direct light spectrally separated by monochromators in the excitation spectral device 500 into input A of Block 610. Alternatively the inputs can be reconfigured by switching fibers 522 and 532. This switching may be accomplished manually. The emission light is gathered by fibers 731 and 732 from ports C and D. The placement of fibers 731 and 732 in the exit ports C and D determines the origin of the emission light in the fibers.

Figure 7:
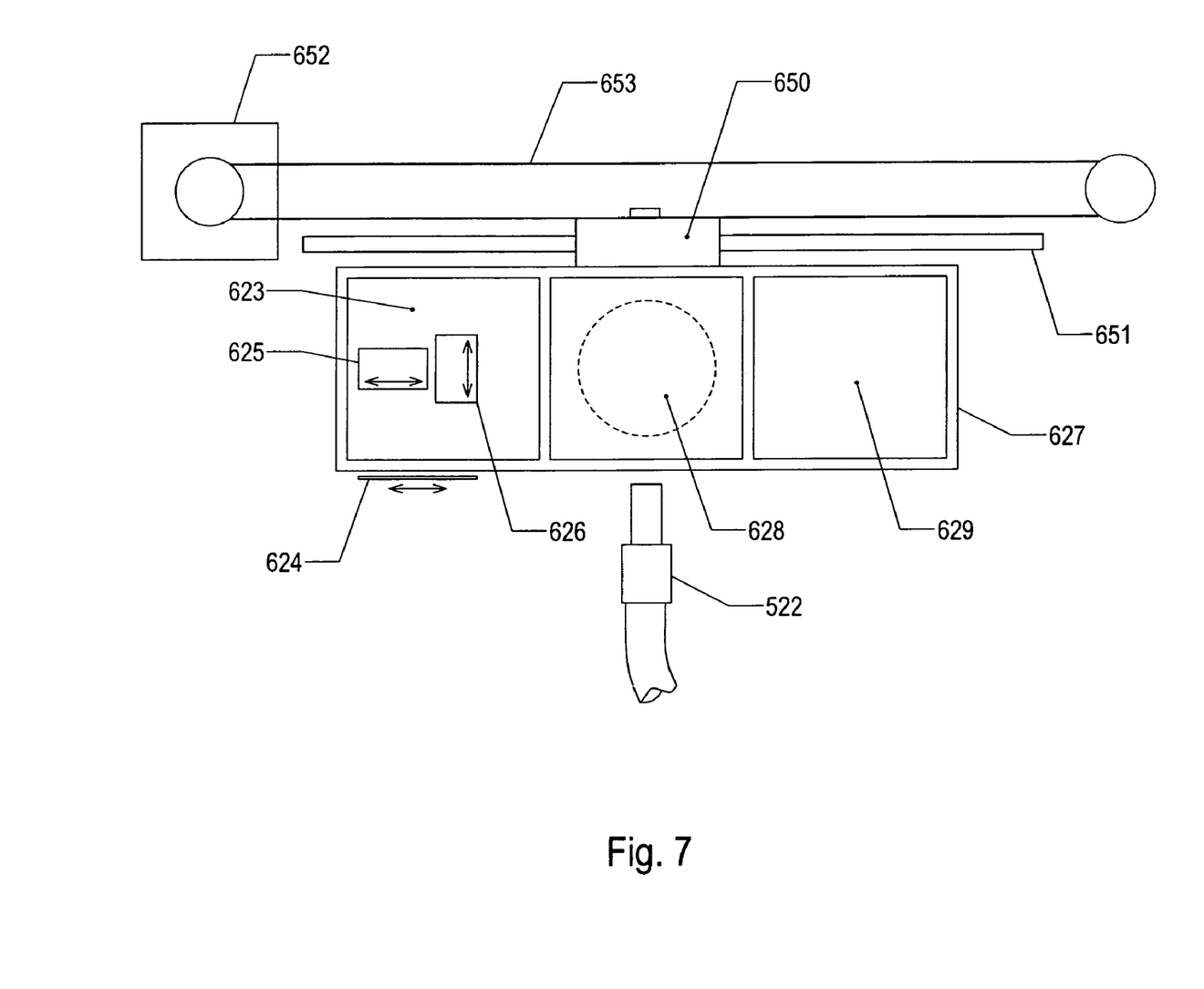
FIG. 7 illustrates a holder according to an exemplary embodiment of the present invention.

FIG. 7 illustrates the holder 627 with associated dichroic mirrors 623, 628, and 629 and linear polarizers 624, 625, and 626 according to an exemplary embodiment of the present invention. The holder 627 is affixed to the slider 650, which slides along rail 651 due to the applied force from the motor 652 through the belt 653. The holder 627 moves in a direction perpendicular to the plane defined by the optical axes of the excitation and emission light. Although two different fibers 522 and 532 could occupy the fiber position depicted in FIG. 7, for the sake of clarity only fiber 522 is shown.

In the depicted design there are five possible positions for the holder 627 relative to the fiber 522, which delivers the excitation light. The first position, which is depicted in FIG. 7, represents a situation where the center of mirror 628 is aligned with the optical axis of the fiber 522. In this position fluorescence polarization based assays cannot be conducted. If the holder 627 is moved to the left for a distance equal to the distance between the centers of mirror 628 and 629, the holder 627 will be in the second position. In the second position, the mirror 629 plays an active role, and fluorescence polarization based assays cannot be conducted.

The three other positions of the holder 627 correspond to three different situations. First, when the right third of the mirror 623 is positioned in front of the fiber 522, fluorescence polarization based assays cannot be conducted. Second, when the middle third of the mirror 623 is positioned in front of the fiber 522, the linear polarizer 624 is in the optical path of the excitation light, and the linear polarizer 626 is in the optical path of the emission light. In this case the polarization vectors of the excitation and emission light are crossed. Third, when the left third of the mirror 623 is positioned in front of the fiber 522, the linear polarizer 624 is still in the optical path of excitation light, and another linear polarizer 625 is in the optical path of the emission light. In this case the polarization vectors of the excitation and emission light are parallel. Thus the linear motion of the holder 627 not only selects which mirror is placed in the optical path, but also allows for fluorescence polarization measurements.

As shown in FIG. 7, the linear polarizers 625 and 626 have parallel surface orientations and perpendicular polarization axis orientations. They have active areas of equal sizes, and each size is comparable to the size of the cross-section of the emission light. The polarization axis of the linear polarizer 624 is parallel to the polarization axis of the linear polarizer 625, and perpendicular to the polarization axis of the linear polarizer 626. The area of the linear polarizer 624 is at least twice the area of the linear polarizer 625. The area of the mirror 623 is at least three time the area of the linear polarizer 625. The mirror 623 is partially reflective and partially transparent.

Figure 8:
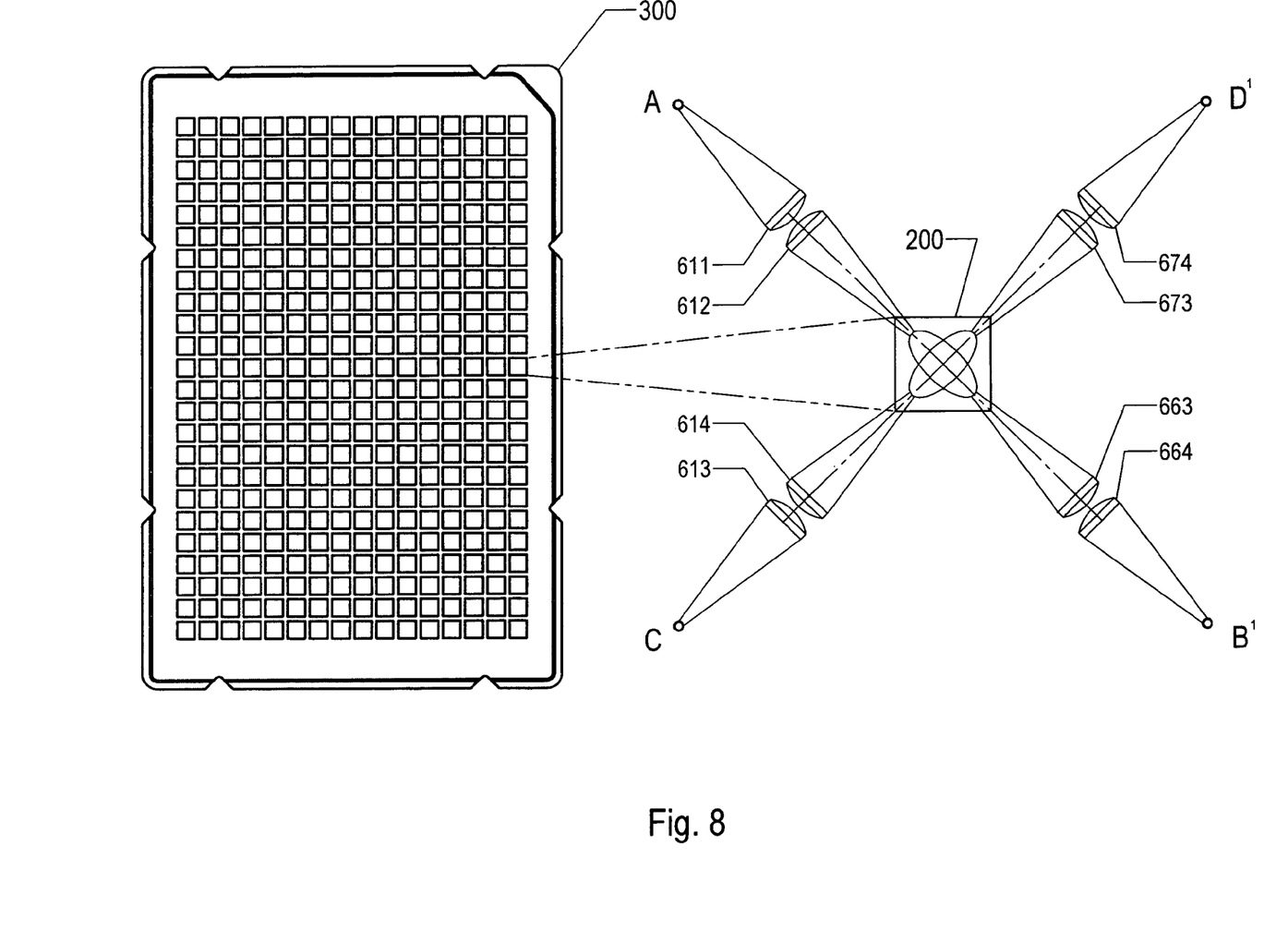
FIG. 8 shows a view of the excitation-emission separation device along vertical axes toward the microplate according to an exemplary embodiment of the present invention.

FIG. 8 shows a view from above the microplate 300, along vertical axes toward the microplate 300 of the block 610 of the excitation-emission separation device 600. Points A and B' are input portals of the excitation-emission separation device 600. Lenses 611, 612, 663, and 664 focus excitation light onto the microwell 200 in the microplate 300. Lenses 613, 614, 673, and 674 collect emission light and focus it into points C and D', which are exit portals of the excitation-emission separation device 600. Standard 384 well microplates have an upper edge with a nearly square shape. The optical axes of lenses 611, 612, 663, 664, 613, 614, 673, and 674 are oriented along the diagonals of microwells 200. Using this arrangement a reading may be taken on the same microwell 200 simultaneously via filter-based or monochromator-based spectral systems. Because the excitation light from point A is reflected toward point B' and vice versa, very little excitation light is reflected toward exit portals C and D'. Therefore, the emission light is spatially separated from the excitation light.

Figure 9:
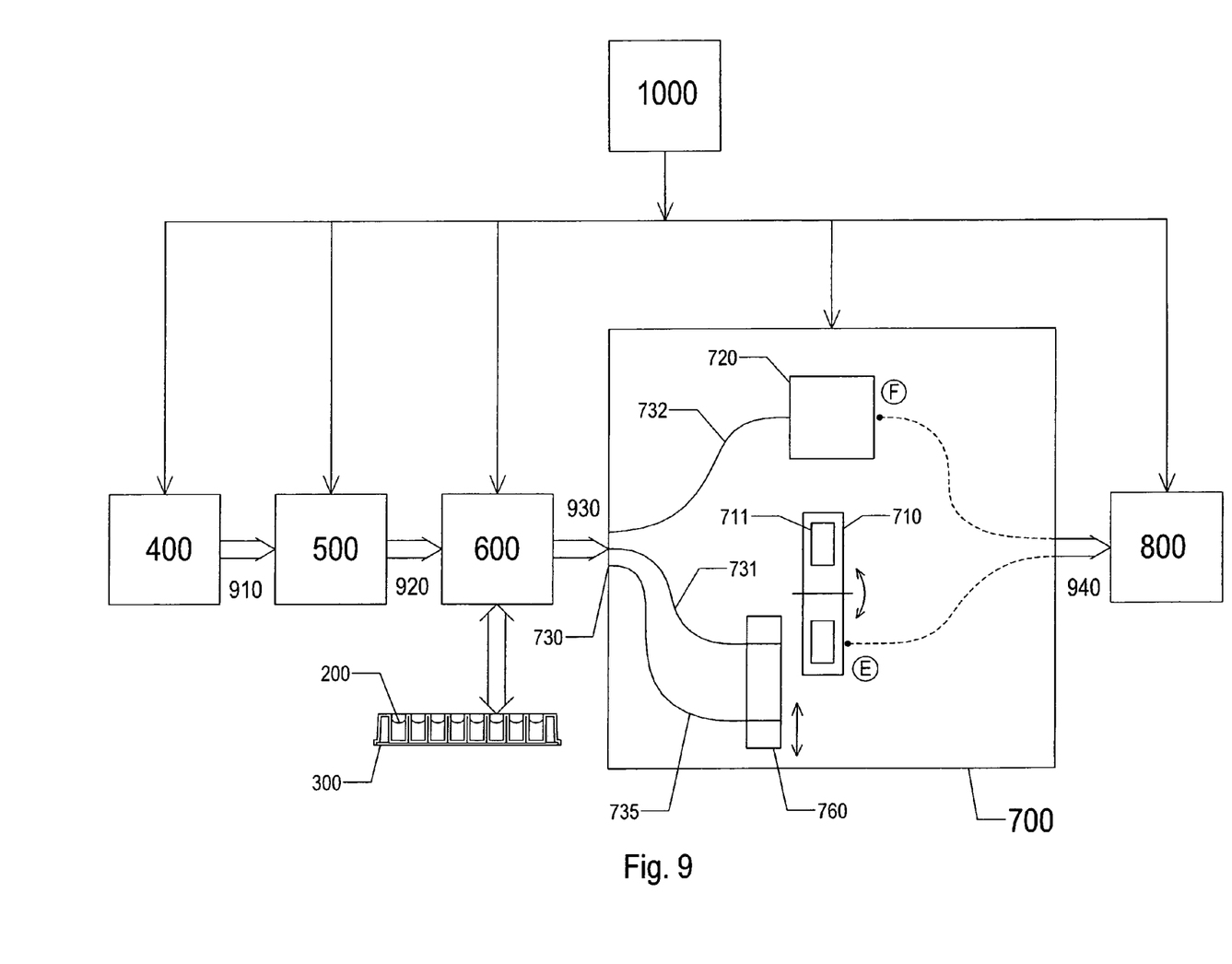
FIG. 9 illustrates an emission spectral device according to an exemplary embodiment of the present invention.

FIG. 9 illustrates the structure of the emission spectral device 700 according to an exemplary embodiment of the present invention. In a preferred embodiment, the emission spectral device 700 has two spectral selection devices, which differ by the physical technology by which they separate light with different wavelengths. The first device is a filter selection device 710, which has a variety of filters 711. The second device is a double monochromator 720. As shown in FIGS. 6 and 9, fibers 731, 732, and 735 extend from their respective locations within the excitation-emission separation device 600 into the emission spectral device 700. The selector switch 760 is used to direct light from fibers to the filter selection device 710. FIG. 9 shows that the fiber 731 from fluorescent measurement block 620 and the fiber 735 from the luminescence measurement block 630 are connected to the selector switch 760. FIG. 9 also shows that the fiber 732 from the fluorescent measurement block 610 is connected to the monochromator 720. However, the arrangement in FIG. 9 is merely exemplary, and a user can change the connections by physically switching the fiber connections within the excitation-emission separation device 600, or within the emission spectral device 700.

In a preferred embodiment, the exit portals of the excitation-emission separation device 600 are in close proximity to the input portal 730 of the emission spectral device 700. Points E and F may represent the exit portals of the emission spectral device 700. The detector 800 may comprise two photomultiplier tubes (PMTs) positioned at points E and F (not shown).

Figure 10:
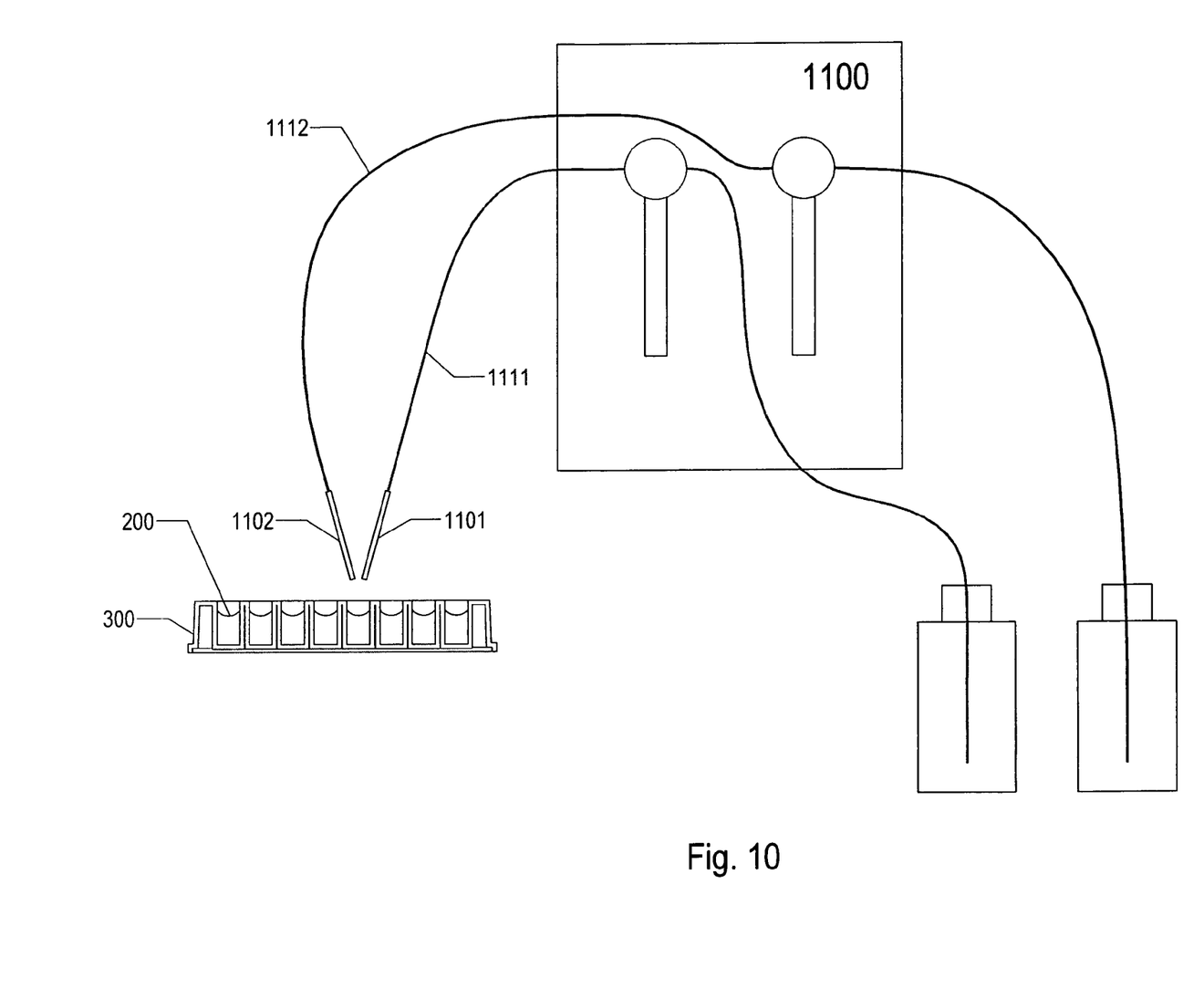
FIG. 10 shows a fluid dispenser according to an exemplary embodiment of the present invention.

FIG. 10 shows a fluid dispenser 1100 according to an exemplary embodiment of the present invention. The purpose of the fluid dispenser 1100 is to inject fluid into microwells 200 to initiate the reaction under investigation. Often the time from initiation to the time measurements have to take place is very short. Therefore, the injection ports 1101 and 1102 may be placed in close proximity to the optical reading system. Further, two separate fluid lines 1111 and 1112 may be used. Each fluid line connects to the stepper motor driven syringe drive for positive displacement fluid delivery. A three-way valve alternately connects a syringe to supply bottles on a suction stroke or to an injector line for dispensing.

As discussed above, exemplary embodiments of the present invention provide a Universal Multidetection System for determining fluorescence, chemiluminescence, and/or light absorbance of a sample in a microplate that allows the user to reconfigure and optimize the measurement system for a particular modality. The Universal Multidetection System allows the user to choose the best measurement method for his assay. The user can select interference filters for their low detection limits and ability to run FP, TRF, and HTRF measurements with state of the art results, dual monochromators for their wavelength flexibility and spectral scanning, or a combination of both filters and monochromators. Both the excitation spectral device 500 and the emission spectral device 700 may contain interchangeable filter systems and monochromators.

In addition to providing unmatched flexibility, the Universal Multidetection System also opens an avenue to run experiments that were not previously possible. For example, in the fluorescence mode, when only a small amount of an unknown fluorofore is available and it is not possible to increase the signal in the monochromator-based system by increasing the sample concentration, the user can obtain rough excitation and emission scans by using monochromators 530 and 720 in the excitation spectral device 500 and the emission spectral device 700, respectively. Based on these initial excitation and emission scans, the user can then select an appropriate filter 521 to excite the sample with light that causes much stronger emission from the sample. The stronger emission spectrum can then be re-recorded. The user can also select a filter 711 to replace the emission monochromator 720 and re-record the excitation spectrum. It is important to have high-quality measurements of both the excitation spectrum and the emission spectrum. This process increases the emission signal and the signal-to-noise ratio, resulting in improved excitation and emission spectra, as compared with spectra obtained with just a monochromator-based system. It also allows a user to work with an unknown sample, and optimize the measurement conditions for that sample.

This approach can also be used to achieve maximum sensitivity in end-point reads. The user can select particular excitation wavelengths by using a monochromator 530 in the excitation spectral device 500, and transmit the emission light through a filter 711 in the emission spectral device 700. A similar benefit can be obtained by using a filter 521 in the excitation spectral device 500 with a monochromator 720 in the emission spectral device 700 during an end-point read. These methods are particularly suited to enhancing performance of environmentally sensitive labels, where variations in conditions give rise to perturbations of excitation or emission spectra, such as ion sensitive probes, pH sensitive probes, spectral shifts in polar dyes with conjugation, and binding and membrane probes.

Exemplary embodiments of the present invention have been described for illustrative purposes, and those skilled in the art will appreciate that various modifications, additions and substitutions are possible without departing from the scope and spirit of the invention as disclosed in the accompanying claims. Therefore, the scope of the present invention should be defined by the appended claims and their legal equivalents.

What is claimed is:

1. An apparatus for optically analyzing a sample, comprising:
    a first optical device that transmits a narrow waveband of light;
    wherein the first optical device comprises a first filter and a first monochromator that provide different paths for the narrow waveband of the light.

2. The apparatus of claim 1, wherein the first filter and the first monochromator provide alternative paths for the narrow waveband of the light.

3. The apparatus of claim 1, further comprising:
    a light source that generates the light as broadband excitation light, wherein the first optical device transmits a narrow waveband of the broadband excitation light and blocks other wavebands of the broadband excitation light through a selected one of the first filter and the first monochromator;
    a second optical device that directs the narrow waveband of the broadband excitation light onto the sample and receives emission light from the sample;
    a third optical device that transmits a narrow waveband of the emission light; and
    a detector that converts the narrow waveband of the emission light into an electrical signal;
    wherein the third optical device comprises a second filter and a second monochromator that provide alternative paths for the narrow waveband of the emission light.

4. The apparatus of claim 3, further comprising a controller which stores and analyzes the electrical signal, computes a parameter which characterizes an efficiency of the analysis, and sends a command to at least one of the light source, the first optical device, the second optical device, the third optical device, and the detector;
    wherein the command prompts the at least one of the light source, the first optical device, the second optical device, the third optical device, and the detector to change an internal parameter.

5. The apparatus of claim 3, further comprising a microplate that holds the sample.

6. The apparatus of claim 5, further comprising a dispenser that injects fluid into the microplate.

7. The apparatus of claim 3, wherein the second optical device comprises:
    a holder that moves in a direction perpendicular to optical axes of the broadband excitation light and the emission light;
    a first linear polarizer with a polarization axis perpendicular to the optical axes of the broadband excitation light and the emission light;
    a second linear polarizer with a polarization axis parallel to the optical axes of the broadband excitation light and the emission light;
    a third linear polarizer with a polarization axis parallel to the polarization axis of the first linear polarizer; and
    a partially reflective and partially transparent mirror that directs the excitation light toward a sample and receives the emission light from the sample;
    wherein the holder can be moved to position at least one of the first linear polarizer, the second linear polarizer, the third linear polarizer, and the mirror in a path of at least one of the excitation light and the emission light.

8. The apparatus of claim 3, wherein the light source comprises:
    a first parabolic reflector that collimates light from a first lamp;
    a second parabolic reflector that collimates light from a second lamp;
    a lens that focuses the collimated light from the second lamp onto an exit portal; and
    an off-axis parabolic reflector that focuses the collimated light from the first lamp onto the exit portal;
    wherein the off-axis parabolic reflector moves out of an optical path of the collimated light from the second lamp if the second lamp is emitting light.

9. The apparatus of claim 3, wherein the second optical device comprises:
    a first lens that directs the narrow waveband of the broadband excitation light onto a sample; and
    a second lens that receives the emission light from the sample;
    wherein optical axes of the first lens and the second lens form a V shape in which the sample is positioned at a bottom of the V shape.

10. The apparatus of claim 9, further comprising:
    a third lens that directs a second narrow waveband of broadband excitation light onto the sample; and
    a fourth lens that receives a second emission light from the sample;
    wherein optical axes of the third lens and the fourth lens form a V shape in which the sample is positioned at a bottom of the V shape; and
    none of the optical axes of the first lens, the second lens, the third lens, and the fourth lens are parallel to each other.

* * * * *